United States Patent [19]
Caccavo, Jr. et al.

[11] Patent Number: 5,739,028
[45] Date of Patent: Apr. 14, 1998

[54] CHROMIUM (VI)-RESISTANT STRAIN OF SHEWANELLA ALGA

[75] Inventors: Frank Caccavo, Jr.; Michael J. McInerney, both of Norman, Okla.

[73] Assignee: The Board of Regents of the University of Oklahoma, Norman, Okla.

[21] Appl. No.: 461,332

[22] Filed: Jun. 5, 1995

Related U.S. Application Data

[62] Division of Ser. No. 368,454, Jan. 4, 1995.

[51] Int. Cl.$^6$ .................................. C12P 1/20; C12P 3/00
[52] U.S. Cl. .................... 435/252.1; 435/168; 435/170; 435/822
[58] Field of Search ..................... 435/822, 170, 435/168, 252.1

[56] References Cited

U.S. PATENT DOCUMENTS

| | | | |
|---|---|---|---|
| 5,246,841 | 9/1993 | Yazawa et al. | 435/134 |
| 5,324,491 | 6/1994 | Lovley | 423/11 |
| 5,328,689 | 7/1994 | Weiner et al. | 424/115 |

OTHER PUBLICATIONS

Urone, P. F.; "Stability of Colorimetric Reagent for Chromium, s-Diphenylcarbazide, in Various Solvents", 1955, *Anal. Chem.*, 27 (8):1354–1355.

Hobbie, J. E., et al.; "Use of Nuclepore Filters for Counting Bacteria by Fluorescence Microscopy", May 1977, *Appl. Environ. Microbiol.*, 33(5):1225–28.

Bopp, L. H. and Ehrlich, H. L.; "Chromate Resistance and Reduction in *Pheudomonas fluorescens* strain LB300", *Arch. Microbiol.*, 150:426–431.

Lovley, D. R. and Phillips, E. J.; "Novel Mode of Microbial Energy Metabolism: Organic Carbon Oxidation Coupled to Dissimilatory Reduction of Iron or Manganese", 1988, *Appl. Environ. Microbiol.*, 54 (6):1472–1480.

Wang, P. C., et al.; "Isolation and Characterization of an *Enterobacter cloacae* Strain That Reduces Hexavalent Chromium under Anaerobic Conditions", 1989, *Appl. Environ. Microbiol.*, 55 (7):1665–1669.

Komori, K., et al.; "Effects of Oxygen Stress on Chromate Reduction in *Enterobacter clocae* Strain HO1", 1990, *Journal of Fermentation & Bioengineering*, 69 (1):67–69.

Ohtake, H., et al; "Bacterial Reduction of Hexavalent Chromium: Kinetic Aspects of Chromate Reduction by *Enterobacter cloacae* HO1", 1990, *Biocatalysis*, 4:227–235.

Fujii, E., et al.; "Bacterial Reduction of Toxic Hexavalent Chromium Using a Fed–Batch Culture of *Enterobacter cloacae* Strain HO1", 1990, *Journal of Fermentation and Bioengineering*, 69(6):365–367.

Caccavo, F., Jr., et al.; "A Hydrogen–Oxidizing, Fe(III)–Reducing Microorganism from the Great Bay Estuary, New Hampshire", 1992, *Appl. Environ. Microbiol.* 58(10):3211–3216.

Lovley, D.R.; "Dissimilatory Metal Reduction", 1993, *Annu. Rev. Microbiol.*, 47:263–290.

Lovley, D. R., and Phillips, E. J. P.; "Reduction of Chromate by *Desulfovibrio vulgaris* and its $C_3$ Cytochrome", 1994, *Appl. Environ. Microbiol.*, 60(2):726–728.

Caccavo, Jr., et al.; "*Geobacter sulfurreducens* sp. nov., a Hydrogen–and Acetate–Oxidizing Dissimilatory Metal–Reducing Microorganism", 1994, *Appl. Environ. Microbiol.*, 60 (10):3752–2759.

*Primary Examiner*—Herbert J. Lilling
*Attorney, Agent, or Firm*—Dunlap & Codding, P.C.

[57] ABSTRACT

A chromium-resistant strain of *Shewanella alga* BrY and method of using such for removing chromium (VI) from a chromium-contaminated waste stream involving treating the waste stream with the chromium-resistant strain under anaerobic conditions whereby Cr(VI) in the waste stream is reduced, the chromium generally forming a precipitate which can be separated from the waste stream.

1 Claim, 6 Drawing Sheets

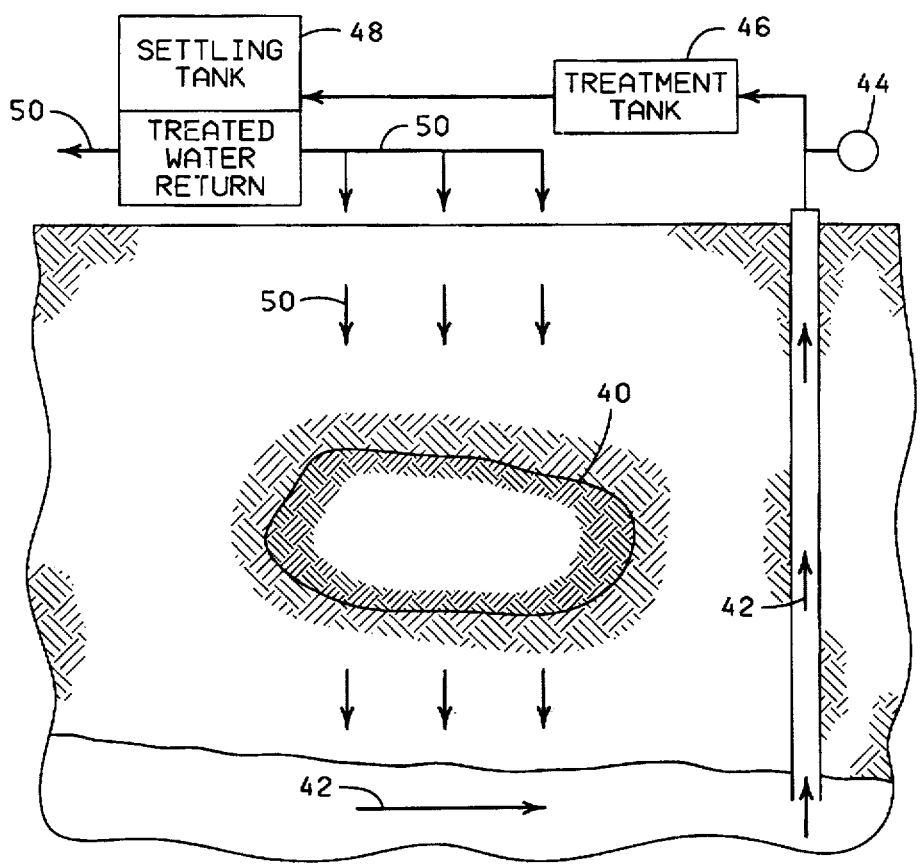
FIG. 10
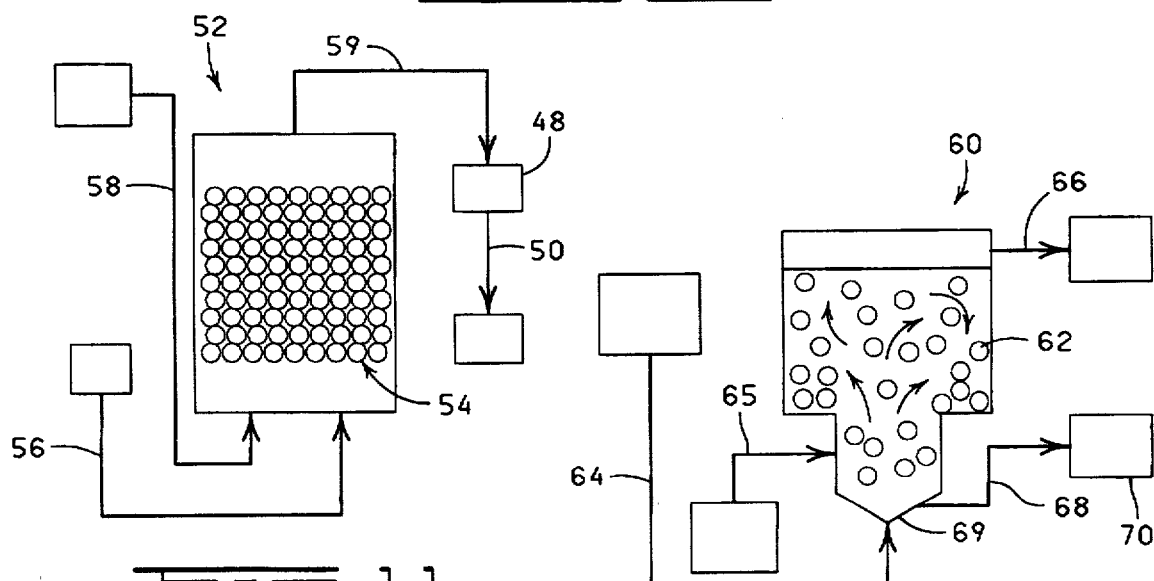
FIG. 11
FIG. 12

CHROMIUM (VI)-RESISTANT STRAIN OF *SHEWANELLA ALGA*

CROSS REFERENCE TO RELATED APPLICATIONS

The present application is a divisional of U.S. Ser. No. 08/368,454, filed Jan. 4, 1995, entitled "METHOD FOR BACTERIAL REDUCTION OF CHROMIUM (VI)".

BACKGROUND

The present invention relates to a method for reducing chromium (VI) and more particularly to a method using a chromium (VI)-resistant dissimilatory bacterial strain to reduce chromium (VI).

Hexavalent chromium (Cr(VI)) is a common toxic heavy metal pollutant in wastewaters and soils and elsewhere in natural ecosystems. Wastewaters containing Cr(VI) are produced by many industrial processes including chromium plating, metal cleaning and processing, wood preparation and alloy preparation. These wastewaters must be treated before being discharged into the environment. Chromium is also used in production of pigments, tanned leathers, fungicides, corrosion inhibitors in cooling water and drilling muds, wall paper, photographic films, magnetic tapes, printing inks and as a catalyst in the synthesis of many organic chemicals. Leakage, poor storage and improper disposal practices have released chromium into the environment in numerous locations causing contamination of ground and surface waters and of soils. These chromium-contaminated sites are subject to remediation requirements to reduce or eliminate the toxic levels of chromium.

As a result, efficient methods for cleaning up waste streams and for remedial clean up of contaminated sites are of critical importance. Conventional methods for removing toxic Cr(VI) ions include chemical reduction followed by precipitation, ion exchange and adsorption on coal activated carbon, alum, kaolinite, and fly ash. Most of these methods require high levels of energy or large quantities of chemical reagents. Other remediation methods involve the use of microorganisms such as the strain HO1 of *Enterobacter cloacae* which can anaerobically reduce Cr(VI) (Komori, K.; Kiyoshi, T.; and Hisao, O.; "Effects of Oxygen Stress on Chromate Reduction in *Enterobacter cloacae* Strain HO1", 1990, *Journal of Fermentation and Bioengineering*, 69(1) :67–69). The Enterobacter strain HO1 can reduce Cr(VI) at levels of around 1–2 mM of potassium chromate, but levels above 5 mM are lethal to the bacteria. Some strains of Pseudomonas and Aeromonas which are capable of reducing Cr(VI) have also been identified.

Although some bacteria apparently use Cr(VI) as a terminal electron acceptor, it is not apparent that Cr(VI) reduction yields sufficient energy to support their anaerobic growth and reproduction. Although organisms such as *Pseudomonas chromatophila* (Lebedeva, E. V. and Lyalikova, N. N. "Reduction of crocoite by *Pseudomonas chromatophila* sp. nov.", 1979, *Microbiology* 48:517–522), *Pseudomonas fluorescens* (Bopp, L. H. and Erlich, H. L. "Chromate resistance and reduction in *Pseudomonas fluorescens* strain LB300", 1988, *Arch. Microbiol.* 150:426–431), and *Enterobacter cloacae* strain HO1 (Ohtake, H., Fujii, E., and Toda, K. "Bacterial reduction of hexavalent chromium: Kinetic aspects of chromate reduction by *Enterobacter cloacae* HO1", 1990, *Biocatalysis* 4:227–235; and Wang, P., Mori, T., Komori, K., Sasatsu, M., Toda, K. and Ohtake, H. "Isolation and characterization of an *Enterobacter cloacae* strain that reduces hexavalent chromium under anaerobic conditions", 1989, *Appln. Environ. Microbiol.* 55:1665–1669), can reduce Cr(VI) anaerobically, no evidence for Cr(VI)-dependent growth has been presented (Lovley, D. R. "Dissimilatory metal reduction", 1993, *Ann. Rev. Microbiol.* 47:263–291).

The application of Cr(VI)-reducing bacteria such as *Enterobacter cloacae* and *Desulfovibrio vulgaris* has been proposed as a potential means of treating Cr(VI)-containing waters and waste streams. However, *D. vulgaris* cannot grow with Cr(VI) as an electron acceptor, and thus treatment systems using this organism would require continual reinoculation. Further, *E. cloacae* requires a rich, expensive, heterotrophic medium in order to reduce Cr(VI), limiting the cost-effectiveness of its use in Cr(VI) treatment systems.

*Shewanella alga* strain BrY is an obligately respiratory, facultatively anaerobic bacterium which can grow anaerobically by coupling the oxidation of organic acids or $H_2$ to the reduction of Fe(III), Mn(IV), U(VI), (Caccavo, Jr. F., R. P. Blakemore, R. P. and Lovley, D. R. "A hydrogen-oxidizing Fe(III)-reducing microorganism from the Great Bay Estuary, New Hampshire ", 1992, *Appl. Environ. Microbiol.* 58:3211–3216), or Co(III)-EDTA. Further, strain BrY contains an electron transport chain and terminal reductase which can couple the oxidation of lactate or $H_2$ to the reduction of Cr(VI) as well. However, all attempts to grow this organism with Cr(VI) as the sole terminal electron acceptor have heretofore been unsuccessful. Similar results have been observed with *Desulfovibrio vulgaris* (Lovley, D. R. and Phillips, E. J. P. "Reduction of chromate by *Desulfovibrio vulgaris* and its c3 cytochrome", 1993, *Appl. Environ. Microbiol.* 60:726–728).

Identification of a bacterial strain not only resistant to high levels of Cr(VI) but which could also use Cr(VI) as a terminal electron acceptor in a process yielding sufficient energy to sustain continuous growth in situ would be a valuable means of purifying Cr(VI)-containing soils, waters, and waste streams.

BRIEF DESCRIPTION OF THE DRAWINGS

FIG. 10 shows a groundwater pumping type treatment system.

FIG. 11 shows a packed-bed type treatment tank.

FIG. 12 shows a fluidized-bed type treatment tank.

DESCRIPTION OF THE INVENTION

Figure 1:
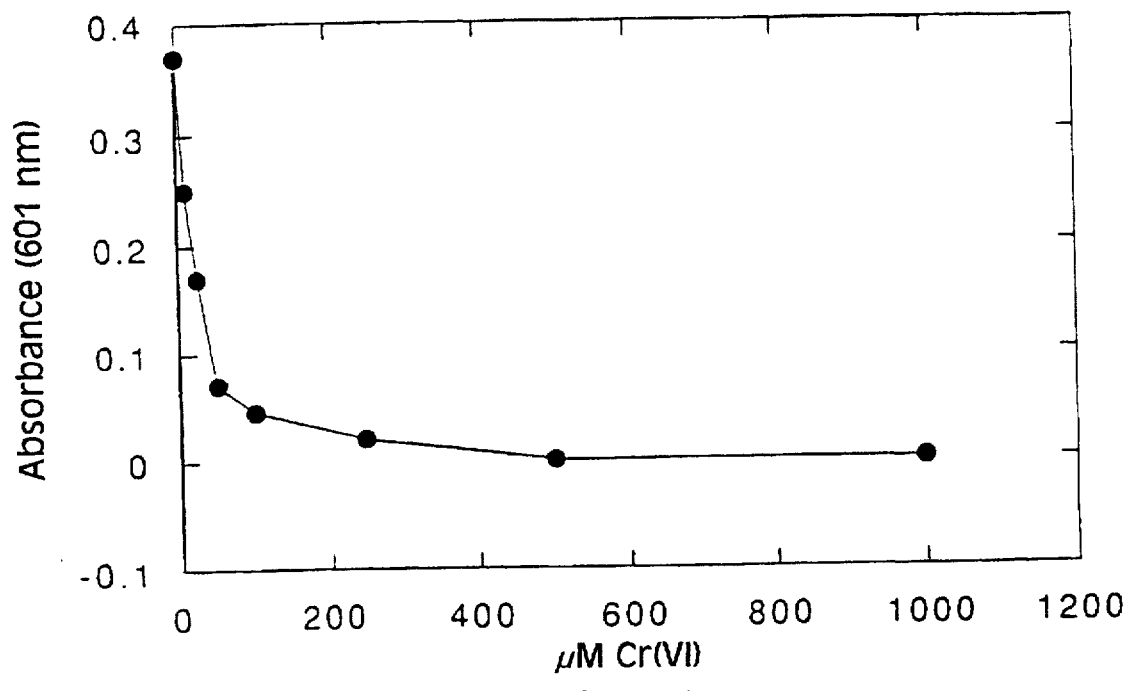
FIG. 1 shows growth of wild-type strain BrY under varying concentrations of Cr(VI) under aerobic conditions.

Identified herein is Cr(VI)-resistant mutant strain of BrY which can gain energy to support anaerobic growth by Cr(VI) reduction. The Cr(VI)-resistant mutant can be used in a variety of methods for remediating Cr(VI)-contaminated soils, waters or waste streams. When the chromium-reducing microorganisms described herein are placed in waters, soils or other waste streams containing dissolved Cr(VI), the Cr(VI) is reduced to Cr(III) which forms a precipitate which can then be removed.

In one version, the method of the present invention can be carried out in a bioreactor comprising any variety of culture vessels in which the organisms are attached to a stationary substrate (e.g., a packed-bed) or are free-floating or are attached to free-floating substrates (e.g., a fluidized-bed). If necessary, an electron donor and/or nutrient medium are added to the reactor. The chromium-containing water is introduced into the bioreactor wherein the Cr(VI) is reduced and forms a precipitate which can be more easily concentrated and removed from the system, for example, by filtration.

In another version, the chromium-reducing bacteria may be disposed in a container compartment where they are separated from chromium-contaminated water disposed therein by a semipermeable membrane. The chromium (VI) in the water can diffuse across the membrane and into the compartment containing the bacteria where the Cr(VI) is reduced and precipitated out. In another embodiment, the bacteria may be attached to a support material within a column through which contaminated water can pass and where chromium (VI) can be reduced when the Cr(VI)-contaminated water is passed into the column.

It is also contemplated that the BrY-MT strain disclosed herein can be used to treat chromium-contaminated ground water in situ by injecting the microorganisms, along with a suitable electron donor if necessary, into a specific "injection zone" of the subsurface. As groundwater passes through the injection zone, further movement of chromium is inhibited by the precipitation of Cr(VI) effected by the bacteria. In another version, the bacteria could be injected into the injection zone within semipermeable membrane containers. After a period of time in which the microorganisms reacted with the chromium in the groundwater, the semi-permeable containers could be removed from the injection zone, thereby removing reduced chromium from the subsurface zone.

It is also contemplated that the strain of Shewanella alga described herein may be used to treat waste streams contaminated with Fe(III), Mn(IV), and U(VI) for the purpose of reducing these forms to a lower oxidation state.

More particularly, the present invention contemplates a method of reducing Cr(VI) concentration in a waste stream under anaerobic conditions. In one version the invention comprises the steps of providing a culture of a Cr(VI)-resistant mutant strain of a first Shewanella alga strain, and treating the waste stream with the mutant strain under anaerobic conditions wherein at least a portion of the Cr(VI) in the waste stream is reduced by the mutant strain forming a chromium precipitate. The method may comprise the additional step of separating the chromium precipitate from the waste stream.

The culture may be provided in a compartment having a semipermeable membrane accessible to the waste stream wherein the Cr(VI) is able to pass from the waste stream through the semipermeable membrane to the culture. The method may further comprise the step of adding an electron donor to the culture. The electron donor may be selected from the group consisting of hydrogen, lactate, formate, and pyruvate. The culture may be attached to a solid substrate in a container wherein the waste stream is exposed to the culture by passing the waste stream into the container. The solid substrate may be a packed bed or a fluidized bed. In the step of providing a mutant strain, the mutant may be the strain having ATCC accession number 55627. In the step of providing a mutant strain, the first Shewanella alga strain may be strain BrY having ATCC accession number 51181. In the step of providing a mutant strain, the mutant strain may be obtained by isolating the mutant strain after a series of sequential transfers into media having successively higher concentrations of Cr(VI).

In another version of the present invention, the method comprises the steps of (1) providing a Cr(VI)-resistant microorganism able to reduce Cr(VI) and which can persist as a sustainable population in the presence of Cr(VI), (2) providing a medium comprising an electron-donor utilizable by the Cr(VI)-resistant microorganism, and (3) treating the waste stream with the microorganism and with the medium under anaerobic conditions wherein at least a portion of the Cr(VI) is reduced by the microorganisms to form a chromium precipitate. The method may comprise the additional step of separating the chromium precipitate from the waste stream. The waste stream may comprise a Cr(VI)-contaminated soil. When the waste stream is a soil, the Cr(VI)-contaminated soil may be deposited within a chamber having the microorganism therein and wherein the temperature of the soil within the chamber is held to within a range of from 20° C. to about 50° C. The electron donor may be selected from the group consisting of hydrogen, lactate, formate, and pyruvate.

The invention may further comprise a chromium (VI)-resistant strain of the Shewanella alga strain deposited under ATCC accession number 51181. The invention may further comprise a chromium (VI)-resistant strain of Shewanella alga deposited under ATCC accession number 55627. The invention may further comprise a biologically pure culture of Shewanella alga strain BrY-MT deposited under ATCC accession number 55627. The invention may further comprise a biologically pure culture of a strain of Shewanella alga BrY which is resistant to Cr(VI) and can grow a generally sustainable population under anaerobic conditions in the presence of Cr(VI). The invention may further comprise a biologically pure culture of a strain of Shewanella alga BrY which is resistant to Cr(VI) up to a concentration of at least about 8 mM. The invention may further comprise a biologically pure culture of a strain of Shewanella alga BrY which is resistant to Cr(VI) up to a concentration of at least about 8 mM and which can grow anaerobically with Cr(VI) as the terminal electron acceptor.

MATERIALS AND METHODS

Bacterial strains.

The source strain was a wild type strain of Shewanella alga designated as strain BrY (ATCC accession number 51181). The Cr(VI)-resistant mutant of Shewanella alga identified herein is designated as strain BrY-MT and was deposited with The American Type Culture Collection (ATCC) located at 12301 Parklawn Dr., Rockville, Md., 20852, on Oct. 20, 1994, and has the ATCC accession number 55627.

Media.

Media used for aerobic growth of the bacteria contained in g/L d-$H_2O$:$Na_2HPO_4$, 2.1:$KH_2PO_4$, 1.6:$NH_4Cl$, 1.5; tryptic soy broth, 1.0. Anaerobic growth medium contained in g/L d-$H_2O$: $NaHCO_3$, 2.5; $KH_2PO_4$, 0.6; $NH_4Cl$, 1.5; tryptic soy broth, 1.0; vitamins, 10 ml, minerals, 10 ml. Both aerobic and anaerobic media contained 20 mM lactate as the electron donor. Cr(VI) was added from a sterile stock solution of potassium chromate. Anaerobic medium was made using standard anaerobic techniques described by Caccavo, F. Jr., McInerney, M. J., Davis, M., Stolz, J. F., Lonergan, D. J., and Lovley, D. R. ("*Geobacter sulfurreducens* sp. nov., a Hydrogen- and Acetate-Oxidizing Dissimilatory Metal-Reducing Microorganisms", 1994, *Appl. Environ. Microbiol,* 60:3752–3759). Djenkolic acid and sulfate were added from sterile stock solutions to provide a final concentration of 1.5 mM. All incubations were at 35° C. in the dark. Aerobic cultures were shaken at 150 rpm.

Cr(VI) measurement.

Cr(VI) concentration was analyzed by the sym-diphenylcarbazide method of Urone, P. F. ("Stability of colorimetric reagent for chromium, s-diphenycarbazide, in various solvents", 1955, *Anal. Chem.* 27:1354–1355). Sub-samples (0.5 ml) were withdrawn with a syringe and needle, and added to 10 ml of 0.2 $NH_2SO_4$. Then 0.5 ml of s-diphenylcarbazide reagent was added. Samples were mixed, filtered through a 0.2 μm filter, and measured at an absorbance of 540 nm.

Cr(VI) reductase assays with washed cell suspensions were performed using the following methods. All manipulations were performed in an anaerobic chamber. All buffers were made anaerobic by boiling and cooling under a stream of oxygen-free high purity $N_2$. Late-log-phase cells were harvested anaerobically by centrifugation at 7,000 X g for 20 min at 4° C. and washed twice by resuspending the pellet in anaerobic PIPES [Piperazine-N,N-bis(2-ethanesulfonic acid)] buffer (20 mM, pH 7.0), and recentrifuging. The final pellet was resuspended in 20 ml of anaerobic PIPES buffer (20 mM, pH 7.0). Potassium chromate was added to Balch tubes containing 10 ml of 20 mM PIPES buffer, pH 7.0, from anaerobic, 100 mM stock solutions in 20 mM PIPES buffer, pH 7.0, to provide a final concentration of 500 μM. The assay tubes were sealed with butyl rubber stoppers and aluminum crimps, the headspace was evacuated and replaced with oxygen-free $N_2$, and the tubes were autoclaved for 20 min at 115° C.

Cr(VI) reductase assays were initiated by anaerobically adding 100 μof cell extract and 10 ml of 100% $H_2$ to the assay tube. The assay tubes were shaken gently and placed on their sides at 35° C. Duplicate tubes were used for each analysis. Replicates did not differ from the mean by more than 10%. Negative controls did not contain $H_2$. Cr(VI) reduction activity assays were performed using fixed time point analyses. Cr(VI) reduction rates were linear with time for up to 5 minutes and were proportional to protein concentration.

Growth measurements.

Aerobic cell growth was measured spectrophotometrically at 601 nm. Anaerobic growth was determined by direct cell counts using a modification of the epifluorescent microscopy technique of Hobie, J. E., Dailey, R. J., and Jasper, S. ("Use of nucleopore filters for counting bacteria by fluorescence microscopy", 1977, *Appl. Environ. Microbiol.* 33:1225–1228), as described by Lovley, D. R. and Phillips, E. P. J. ("Novel mode of microbial energy metabolism: organic carbon oxidation coupled to dissimilatory reduction of iron or manganese", 1988, *Appl. Environ. Microbiol.* 54:1472–1480).

Cytochrome analysis.

Dithionite-reduced minus air-oxidized difference spectra of cell-free extracts were obtained using the following methods. Sodium dithionite-reduced-minus-air-oxidized difference spectra were obtained for cell-free extract. Two milliliters of anaerobic, 20 mM PIPES buffer (pH 7.0) were added to 0.5 ml of cell extract in a quartz cuvette with a path length of 1.0 cm. Both the reference cuvette and sample cuvette were air oxidized with a pipette. The sample cuvette was then reduced with sodium dithionite. The difference spectrum was recorded with a double beam spectrophotometer. The concentration of heme c in cell free extracts was determined by subtracting the absorption minimum at 536 nm from the absorption maximum at 551 nm of the dithionite-reduced-minus-air-oxidized difference spectrum ($\epsilon^{551-536}=1.73\times10^{4}M^{-1}cm^{-1}$).

Chromium-Resistant Strain Isolation.

The present invention contemplates a method for culturing a bacterial strain having at least partial resistance to a heavy metal such as Fe(III), Mn(IV), U(VI) or Cr(VI) and then isolating therefrom a mutant strain having a significantly greater resistance to the heavy metal.

In a preferred version, the present invention contemplates isolating a chromium-resistant mutant from *Shewanella alga* strain BrY, a strain which has a partial resistance to chromium Cr(VI) at low concentrations. The process comprises providing a culture of *Shewanella alga* strain BrY. A viable population of BrY cells is then cultured in media at the minimum inhibitory concentration (MIC) of Cr(VI). The minimum inhibitory concentration is the highest concentration of Cr(VI) at which a viable population of the BrY cells can be sustained in culture. Stated another way, the MIC of Cr(VI) is that concentration just below the concentration of Cr(VI) which completely inhibits growth of strain BrY. The MIC of *Shewanella alga* strain BrY is approximately 250 μM. Where used herein, the terms "Cr(VI)-resistant" cells or "chromium-resistant" cells are meant to refer to cells which are able to grow at concentrations of Cr(VI) which are higher than the MIC of Cr(VI) for *Shewanella alga* strain BrY, or higher than the MIC of Cr(VI) for any other strain of *Shewanella alga* which exhibits at least partial resistance to Cr(VI).

After a period of growth at the MIC, a portion of the culture is transferred into another container having therein a medium with a slightly higher Cr(VI) concentration (for example, about 100 μM higher). This process is repeated whereby each succeeding culture is transferred to a medium having an incrementally-higher Cr(VI) concentration. For example, the increment may be 100 μM. After a predetermined number of these transfers into increasingly higher Cr(VI) concentrations, such as after about 8 to 10 transfers, a strain is isolated from the final culture medium.

The final culture-medium from which the mutant strain is removed preferably has a Cr(VI) concentration which is at least about ten times that of the MIC of the original strain. In the case of BrY, the final medium would have a Cr(VI) concentration of at least about 2.5 to 3.0 mM. Ultimately, the mutant strain which is obtained from the sequential culturing process described herein has a MIC which is at least ten times that of the original strain, preferably at least twenty times, and more preferably at least 25 to 30 times greater. Mutant strains having MICs in excess of 30 times the original MIC are most preferable.

The invention contemplates the use of any mutant strain of a *Shewanella alga* which is produced by the isolation method described herein whereby the mutant strain is isolated after a series of sequential transfers into media having successively higher concentrations of Cr(VI). Preferably, the final medium from which the mutant strain is isolated has a Cr(VI) concentration which is at least about a factor of ten greater than the MIC of Cr(VI) of the parent strain of *Shewanella alga*.

Results

Isolation of the Cr(VI)-resistant mutant.

Figure 2:
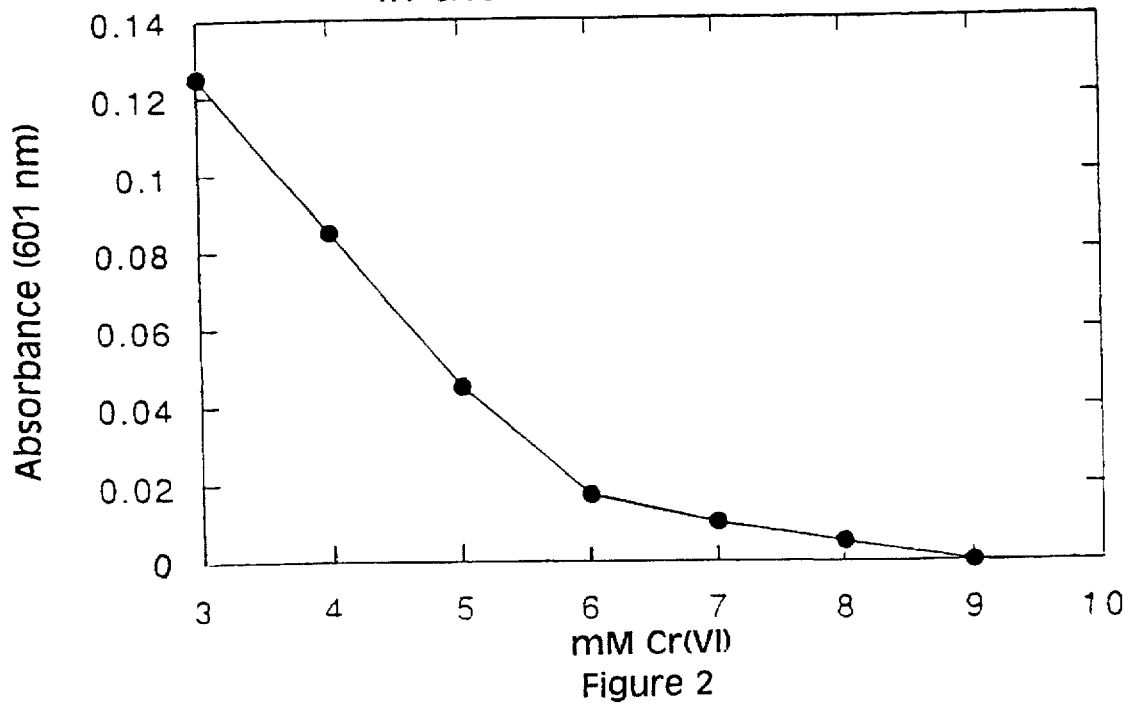
FIG. 2 shows growth of strain BrY-MT under varying concentrations of Cr(VI) under aerobic conditions.

The Minimum Inhibitory Concentration of Cr(VI) for strain BrY was determined to be approximately 250 µM. Strain BrY grew only very slightly at 250 µM Cr(VI) under aerobic conditions (FIG. 1). This culture was continually transferred into an identical medium until dense bacterial growth was observed. This dense culture was then sequentially transferred into a series of aerobic media with Cr(VI) concentrations sequentially increasing in 100 µM increments. A Cr(VI)-resistant mutant, designated herein as strain BrY-MT, was isolated from medium containing 3 mM Cr(VI). This concentration was more than 10 times the MIC for the wild type strain (BrY). The MIC for strain BrY-MT was 8 mM Cr(VI) (FIG. 2). Strain BrY-MT did not lose its resistance to Cr(VI) after 10 transfers in aerobic medium which did not contain Cr(VI).

Cr(VI) reduction by BrY-MT.

Figure 3:
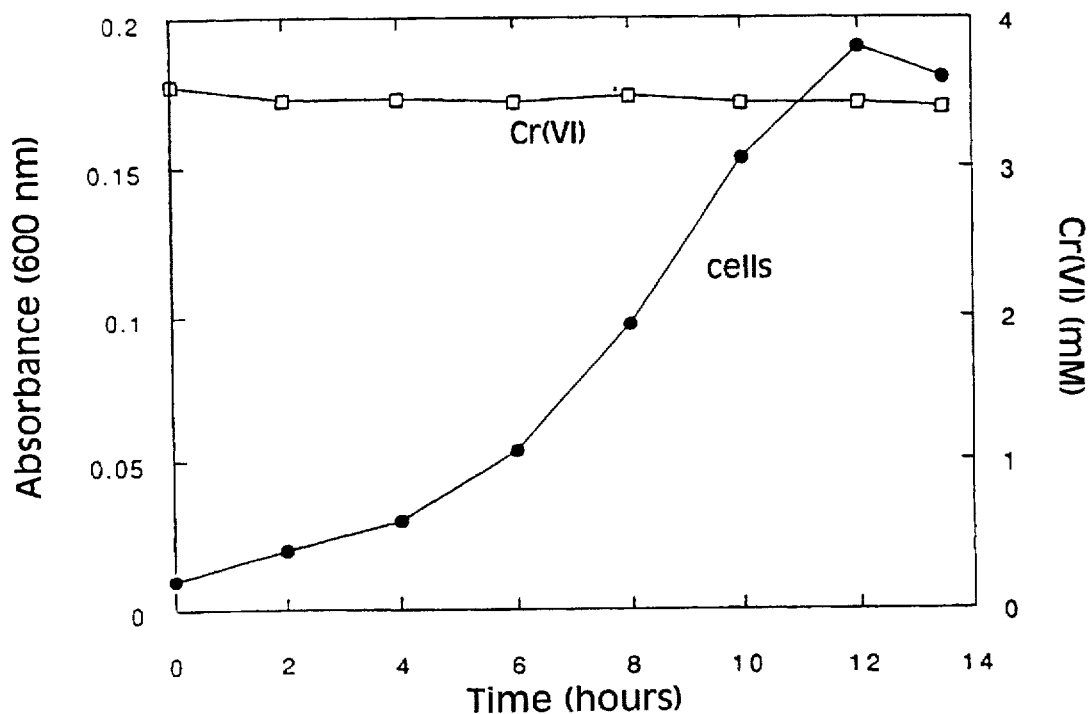
FIG. 3 shows the lack of capability of strain BrY-MT to reduce Cr(VI) under aerobic conditions.
Figure 4:
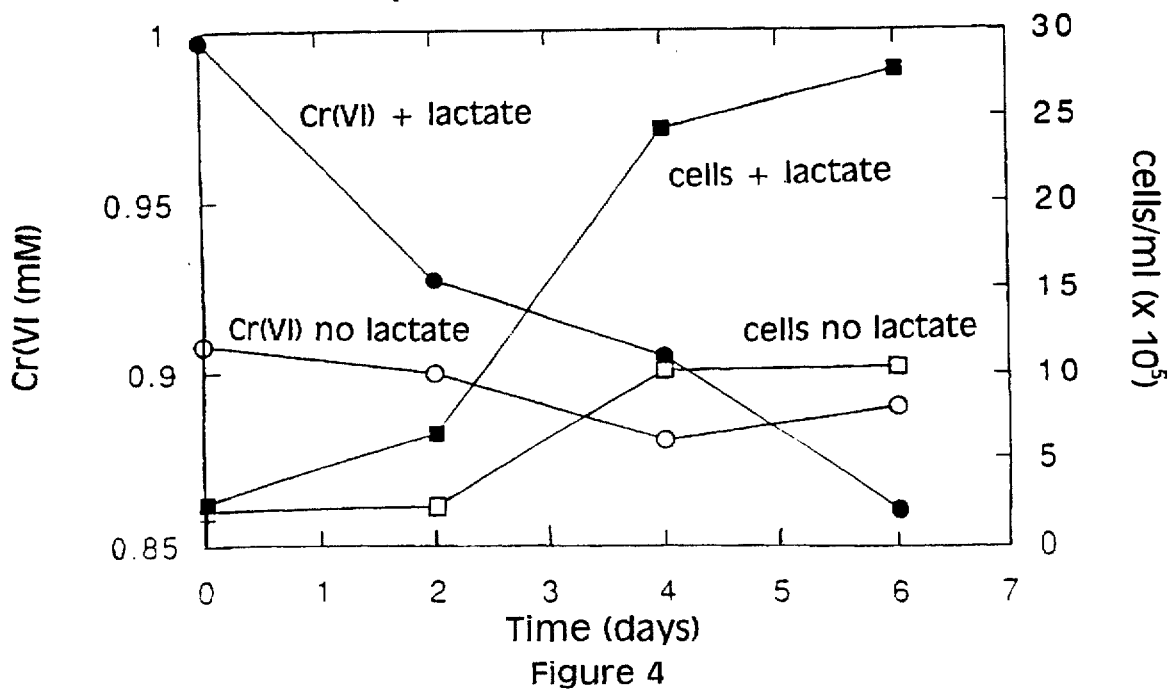
FIG. 4 shows the anaerobic growth of strain BrY-MT using lactate as an electron donor.

Washed cell suspensions of both BrY and BrY-MT strains reduced Cr(VI) with lactate as the electron donor (Table I). Wild type strain BrY did not reduce Cr(VI) under growth conditions, either aerobically or anaerobically. Strain BrY-MT did not reduce Cr(VI) under aerobic growth conditions (FIG. 3), however strain BrY-MT did grow anaerobically by the oxidation of lactate coupled to the dissimilatory reduction of Cr(VI) (FIG. 4). The increase in cell numbers coincided with the decrease in Cr(VI) in the presence of lactate. Only a small amount of Cr(VI) reduction and cell growth was observed in cultures that did not contain lactate. This can be attributed to a small amount of lactate transferred with the inoculum, as cell growth and Cr(VI) reduction stopped when this lactate was depleted.

Repression/derepression assays.

Figure 5:
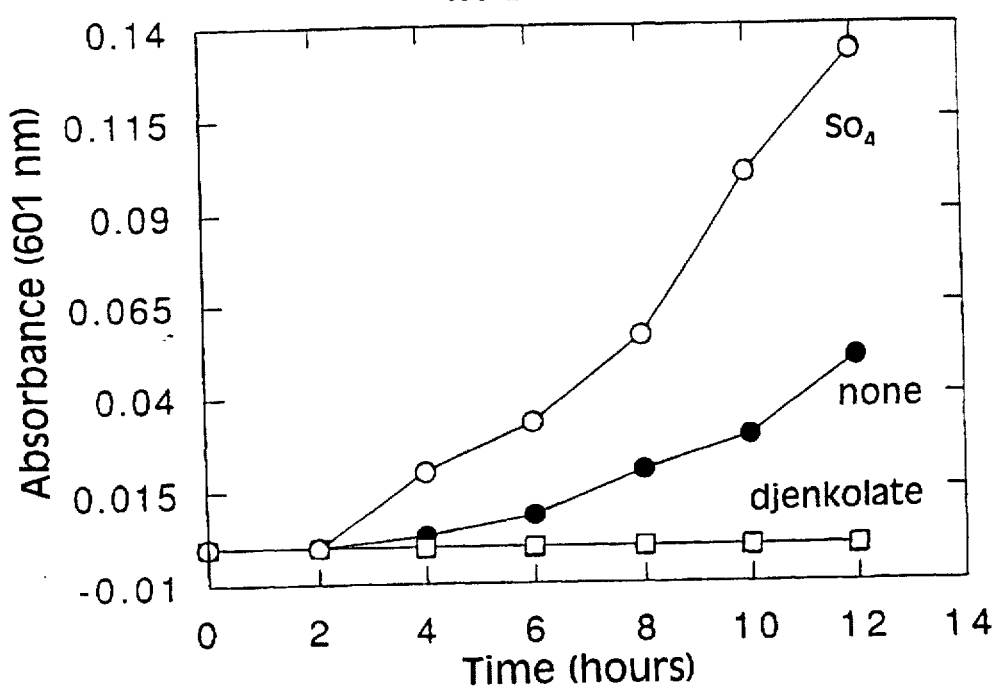
FIG. 5 shows aerobic growth of strain BrY with 100 μM Cr(VI) and $SO_4^{2-}$ or djenkolic acid.
Figure 6:
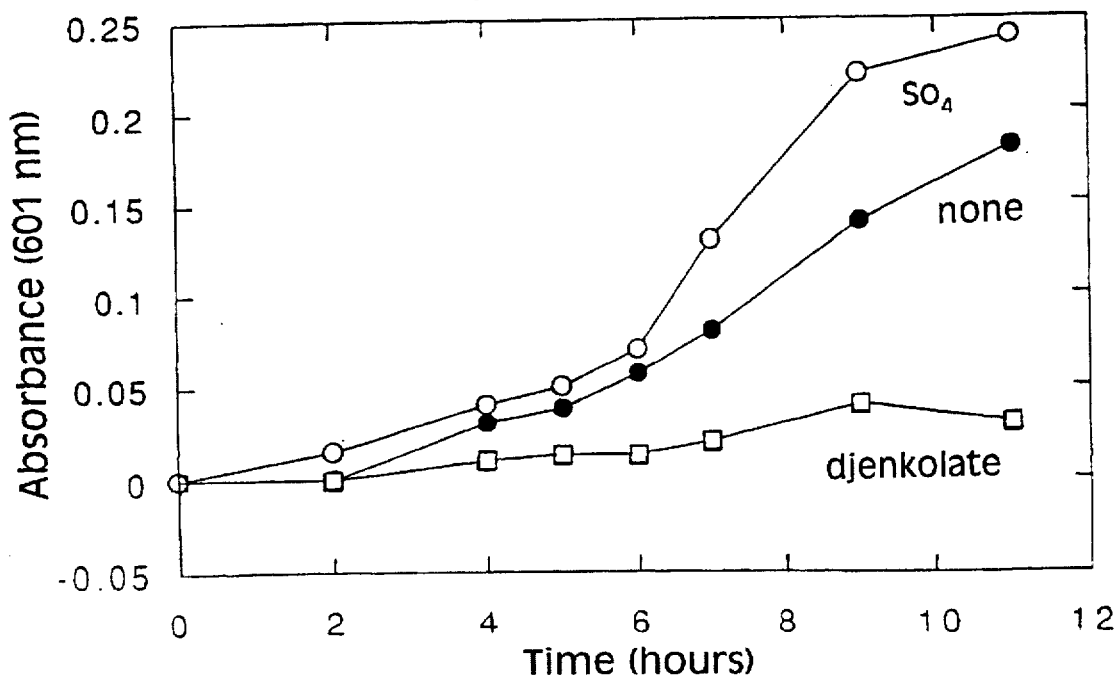
FIG. 6 shows aerobic growth of strain BrY-MT with 3 mM Cr(VI) and $SO_4^{2-}$ or djenkolic acid.

Cr(VI) resistance in both BrY and BrY-MT strains depended on the sulfur source in the medium. Strain BrY grew aerobically with 100 µM Cr(VI) in the medium (FIG. 5). When $SO_4^{2-}$ was also included in the medium, growth was enhanced. When djenkolic acid was included in the medium, growth was inhibited. Growth of strain BrY was not inhibited by djenkolic acid in the absence of Cr(VI), as control cultures reached an O.D. of 0.30 after 12 h of incubation. Similar results were obtained when strain BrY-MT was grown aerobically with 3 mM Cr(VI) (FIG. 6).

Cytochrome analysis.

Figure 7:
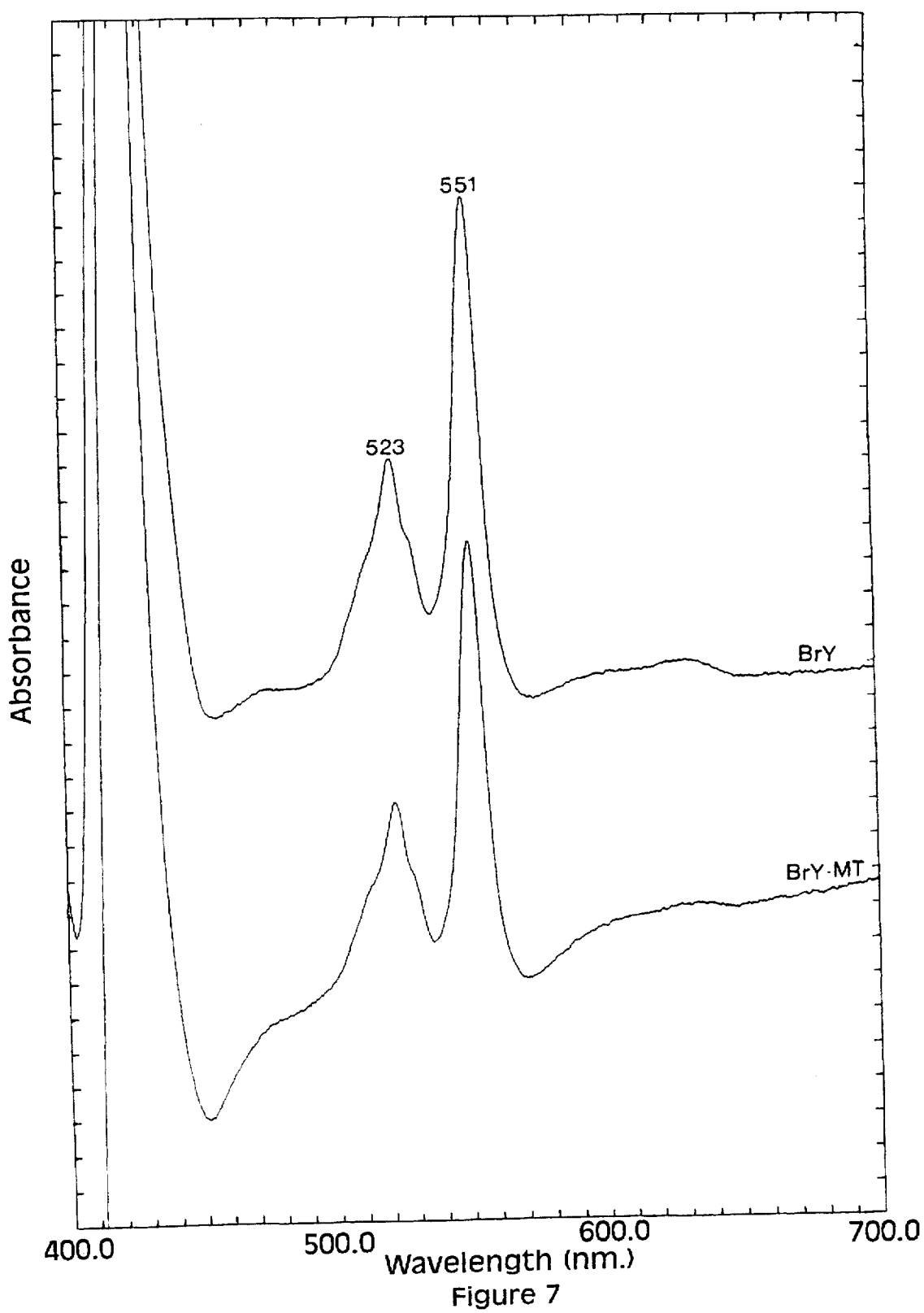
FIG. 7 shows difference spectra of cell-free extracts of strains BrY and BrY-MT.

Difference spectra of cell-free extracts of both strain BrY and strain BrY-MT revealed absorption peaks at 551 nm, 523 nm, and 422 nm (FIG. 7). These peaks are characteristic of c-type cytochromes. Both BrY and BrY-MT contained approximately the same amount of heme c (Table 1).

Cr(VI)-resistant mutant.

Although the dissimilatory metal-reducing microorganism *S. alga* strain BrY produces an electron transport system and terminal reductase that is capable of reducing Cr(VI), Cr(VI) appears to be toxic to the BrY strain under growth conditions. In this study, a Cr(VI)-resistant mutant, strain BrY-MT, was isolated as described above by continually exposing the Cr(VI)-sensitive wild type BrY to gradually increasing amounts of Cr(VI). Strain BrY-MT is resistant to Cr(VI) concentrations at levels more than 30 times the MIC for Cr(VI) of the BrY strain.

Cr(VI)-dependent growth of strain BrY-MT is environmentally significant because it demonstrates that dissimilatory metal-reducing bacteria can reduce toxic and mobile Cr(VI) to less toxic and less mobile forms while sustaining viable Cr(VI)-reducing populations in Cr(VI) contaminated environments.

Bioremediation.

These results demonstrate the *S. alga* strain BrY-MT can grow using Cr(VI) as a sole electron acceptor, and reduce highly toxic and mobile Cr(VI) to less toxic and more immobile forms such as Cr(III) which forms a solid precipitate. Further, these results point out that in situ Cr(VI) bioremediation techniques using dissimilatory metal-reducing bacteria are feasible. Strain BrY-MT can grow upon and reduce Cr(VI), and thus maintain viable populations, in an inexpensive minimal medium. These attributes make strain BrY-MT the organism of choice in in vivo Cr(VI) treatment systems.

*Shewanella alga* strain BrY-MT can be used to diminish Cr(VI) concentrations in chromium-contaminated waste streams such as soils, industrial waste, and surface and groundwaters. Chromium-contaminated soils can be treated ex situ for example.

Figure 8:
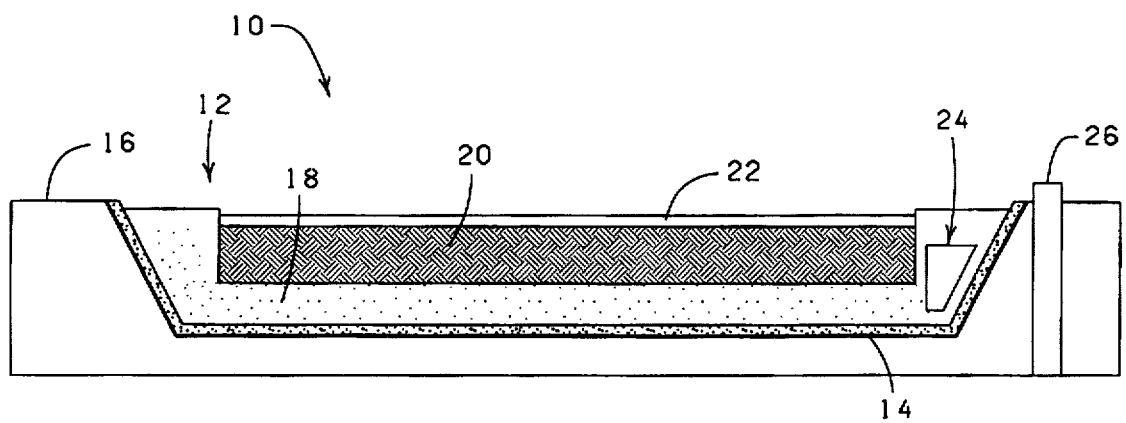
FIG. 8 shows a containment berm-type treatment system.

One version of a soil treatment unit is shown in the treatment facility shown in FIG. 8 designated by the general reference numeral 10. The facility 10 comprises a pit 12 having a liner 14 and surrounded by a containment berm 16. A layer 18 of sand and/or gravel is disposed above the liner 14. A quantity of soil 20 or other solid material which is contaminated with chromium (VI) is disposed within the pit 12 over the sand/gravel layer 18. An inoculum 22 of BrY-MT provided in a liquid medium is then disposed over the contaminated soil 20 and percolates through the soil 20. The inoculum 22 is preferably added at a rate of about $10^6$–$10^8$ cells per gm of soil. A drainage collection sump 24 recovers runoff from the soil 20. A contamination monitoring well 26 may be present for monitoring loss of chromium from the pit 12. Nutrients may be added to the inoculated contaminated soil 18 to enhance activity of the inoculum 22 although preferably sufficient nutrients are present in the soil 20.

Figure 9:
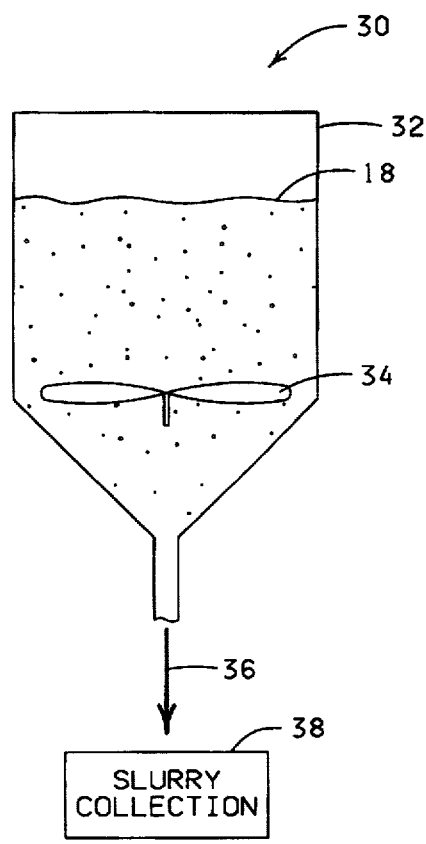
FIG. 9 shows a slurry reactor-type treatment system.

Shown in FIG. 9 and designated by the general reference numeral 30 is another treatment system which can be used to treat soil 20 contaminated with Cr(VI). The system 30 comprises a container 32. The container 32 has a mixing device 34 such as a paddle for mixing contaminated soil which has been inoculated with an inoculum 22 of the Cr(VI)-reducing bacterial strain. Nutrients may be added to enhance activity of the inoculum 22 and water is preferably added to form the treated soil 20 into a slurry 36 which after a period of time for reaction can then be discharged from the reaction container 32. The reacted slurry 36 will then have

TABLE 1

Cr (VI) Reductase Activity and Heme c Content of *S. alga* Strains

| Strain | Total Activity nmoles Cr (VI)/min | Specific Activity nmoles Cr (VI)/min/mg protein | Total Heme c nmoles | Specific Heme c nmoles/mg protein |
|---|---|---|---|---|
| BrY-Wild Type | 1288 | 146 | 35.5 | 1.16 |
| BrY-Mutant | 192 | 29 | 34 | 1.04 | a greatly reduced concentration of Cr(VI). An added benefit of this process is that, contaminated soil can continue to be added to the reaction container 32 as the process is ongoing. The reacted slurry 36 can be collected in a container 38 for further processing or disposal.

Further the temperature and pH conditions can be closely controlled in the container 32 to accelerate the activity of the bacteria. Preferably, the pH of the slurry 36 is maintained below 8. More preferably, the pH of the slurry 36 is maintained at about 7±0.2. The optimum temperature of the system is 35° C.±5°, but may be in a range of from 20°–50° C. Lactate may be added as a carbon source and electron donor. Formate, pyruvate or $H_2$ gas may also be added as an electron donor.

Shown in FIG. 10 is a schematic of a method for treating groundwater which has been contaminated by Cr(VI) in soil. The zone of contaminated soil 40 releases Cr(VI) to the surrounding groundwater 42. The groundwater 42 may be pumped via a pumping system 44 into a treatment tank 46. The treatment tank 46 comprises a system for passing the contaminated water 42 through a bed which sustains a live culture of the Cr(VI) reducing bacteria, as explained in more detail below. The treated water 42 is then sent to a settling tank 48 where the reduced chromium, having formed a solid precipitate, settles from the solution. The treated water 50, which has been substantially cleared of reduced chromium, can then be returned to the environment, for example by being pumped into the soil. The waste product containing the precipitated chromium can be further treated or otherwise disposed of in a manner known to one of ordinary skill in the art.

Versions of a treatment tank of the type which could be used in FIG. 10 are shown in FIGS. 11 and 12. A packed-bed reactor is designated by the general reference numeral 52 in FIG. 11. Contained within the reactor is a high-surface area packed-bed 54 which comprises an inert substrate, such as glass, plastic beads, or activated charcoal, upon which the bacteria can grow.

After a bacterial culture has been established on the packed-bed 54, contaminated water 56 and a nutrient medium 58 are introduced into and circulated within the reactor 52. As noted above, growth conditions of the bacteria can be regulated. As the contaminated water percolates through the packed-bed 54, bacteria act to reduce the Cr(VI). Treated water 59 leaves the reactor 52 and is introduced into a settling tank 48 as described above wherein the precipitated chromium can be removed. The resulting chromium waste product comprises a waste product orders of magnitude less in volume than the original water introduced into the system for treatment.

Shown in FIG. 12 is a fluidized-bead reactor designated by the general reference numeral 60. The fluidized bed comprises a substrate 62 upon which the bacteria can grow as explained above. In this system the contaminated water 64, and optionally nutrient medium 65, is forcibly circulated throughout the bed 62. This circulation process enhances the interaction between the contaminated water and the bacteria upon the bed 62. Treated water 66 flows from one outlet of the system. Nutrients are periodically or continuously introduced into the system to maintain bacterial growth within the reactor 60. As precipitated chromium 68 settles in the sump portion 69 of the reactor 60, it is collected in a collector 70 and removed for further treatment or disposed.

Either of the treatment systems described in FIGS. 11 or 12 could be used in the on-site treatment of industrial waste streams. In another embodiment of the invention, the contaminated soil 40 shown in FIG. 10 could be inoculated in situ for reducing Cr(VI) contamination of the ground water which comes into contact with it as described above.

All publications, references and patents referred to herein are hereby incorporated herein by reference.

Changes may be made in the construction and the operation of the various components, elements and assemblies described herein or in the steps or the sequence of steps of the methods described herein without departing from the spirit and scope of the invention as defined in the following claims.

What is claimed is:

1. A biologically pure culture of a *Shewanella alga* strain resistant to Chromium (VI) under anaerobic growth which is deposited under ATCC accession number 55627.

\* \* \* \* \*

UNITED STATES PATENT AND TRADEMARK OFFICE
CERTIFICATE OF CORRECTION

PATENT NO. : 5,739,028
DATED : April 14, 1998
INVENTOR(S) : Frank Caccavo, Jr. et al.

It is certified that error appears in the above-identified patent and that said Letters Patent is hereby corrected as shown below:

On the title page, item [56], under Other Publications,

"Bopp, L. H. and Ehrlich, H. L.", before "*Arch.*", insert --1988--.

After the "Hobbie, J.E., et al.;" reference, insert:

--Lebedeva, E. V. and Lyalikova, N. N. "Reduction of crocoite by *Pseudomonas chromatophila* sp. nov.", 1979, *Microbiology* 48:517-522--.

| | |
|---|---|
| Col. 2: | line 30, delete "c3" and substitute therefor --$C_3$--. |
| | line 65, after "is" and before "Cr(VI)-resistant", insert --a--. |
| Col. 5: | line 40, delete "µof" and substitute therefor --µl of--. |
| | line 53, delete "Hobie" and substitute therefor --Hobbie--. |
| Col. 9: | line 6, delete "Further" and substitute therefor --Further,--. |

Signed and Sealed this

Seventeenth Day of August, 1999

Q. TODD DICKINSON

*Attest:*

*Attesting Officer*   *Acting Commissioner of Patents and Trademarks*

UNITED STATES PATENT AND TRADEMARK OFFICE
CERTIFICATE OF CORRECTION

PATENT NO. : 5,739,028
DATED : April 14, 1998
INVENTOR(S) : Frank Caccavo, Jr. et al.

It is certified that error appears in the above-identified patent and that said Letters Patent is hereby corrected as shown below:

In the Drawings: Figure 9, delete "18" and substitute --20-- therefor.

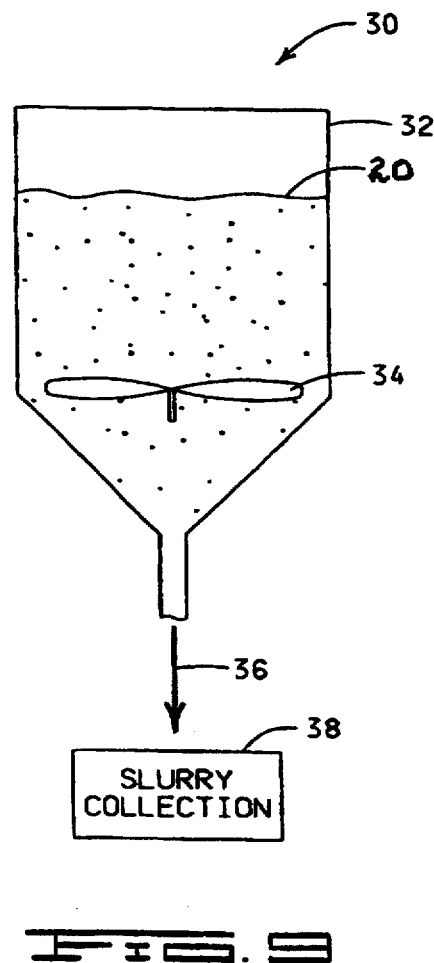

FIG. 9